United States Patent [19]

Rasheed et al.

[11] 4,177,270

[45] Dec. 4, 1979

[54] SOIL FUNGICIDAL (NITROGEN HETEROCYCLIC)-SUBSTITUTED-1,3-BENZODITHIOLE-2-ONES

[75] Inventors: Khalid Rasheed, Weslaco; James D. Warkentin, McAllen, both of Tex.

[73] Assignee: The Ansul Company, Marinette, Wis.

[21] Appl. No.: 860,455

[22] Filed: Dec. 14, 1977

Related U.S. Application Data

[62] Division of Ser. No. 618,255, Sep. 30, 1975, Pat. No. 4,084,954.

[51] Int. Cl.$^2$ ............... A01N 9/22; C07D 265/30
[52] U.S. Cl. ............... 424/248.51; 260/326.25; 260/326.34; 260/326.5 SA; 260/326.83; 424/250; 424/267; 424/274; 544/79; 544/121; 544/129; 544/141; 544/145; 544/160; 544/357; 544/364; 544/372; 544/377; 544/393; 546/187; 546/197; 546/230; 546/233
[58] Field of Search ..... 71/90; 260/293.57, 326.5 SA, 260/326.34, 327 M, 326.25; 424/267, 274, 248.51, 250; 544/145, 357, 377, 79, 121, 129, 141, 364, 372

[56] References Cited

U.S. PATENT DOCUMENTS

| | | | |
|---|---|---|---|
| 2,886,488 | 5/1959 | Berg et al. | 424/276 |
| 3,214,442 | 10/1965 | Klingsberg | 260/327 M |
| 3,444,186 | 5/1969 | Sakai et al. | 260/327 M |
| 3,445,480 | 5/1969 | Allais et al. | 260/327 M |
| 3,455,952 | 7/1969 | Bulbenko et al. | 260/327 M |
| 3,491,119 | 1/1970 | Fields | 260/327 R |
| 3,749,736 | 7/1973 | Diekman | 260/327 M |
| 3,818,041 | 6/1974 | Fields | 260/327 C |

FOREIGN PATENT DOCUMENTS

823251  11/1959  United Kingdom .

OTHER PUBLICATIONS

*Chemical Abstracts*, 85:21185j (1976), [Buza, D. et al., *Rocz. Chem.* 1975, 49(12), 2001–16].
Hurtley, W. et al., *J. Chem. Soc.*, pp. 1821–1828 (1926).
Hunig, S., et al., *Liebigs Ann. Chem.*, 738, 192–194 (1970).
Dallacker, F., et al., *Liebigs Ann. Chem.*, 689, 179–183 (1965).
Shasha, B., et al., *Nature*, 210 (No. 5031), 89–90 (1966).
*Chemical Abstracts*, 60:5665–7 (1964), [Wizinger, I. et al., *Helv. Chim. Acta*, 46(6), 2167–7 (1963)].
*Chemical Abstracts*, 78:16155a (1973), [Feher, F., et al., *Z. Naturforsch.* B 1972, 27(8), 1006–7].

*Primary Examiner*—Alan L. Rotman
*Assistant Examiner*—Richard A. Schwartz
*Attorney, Agent, or Firm*—Morgan, Finnegan, Pine, Foley & Lee

[57] ABSTRACT

1,3-Benzodithiole-2-one and 1,3-benzodithiole-2-thione compounds are disclosed including the novel method of preparing said compounds and their biocidal activity.

9 Claims, No Drawings

SOIL FUNGICIDAL (NITROGEN HETEROCYCLIC)-SUBSTITUTED-1,3-BENZODITHIOLE-2-ONES

CROSS-REFERENCE TO RELATED APPLICATION

This application is a division of application Ser. No. 618,255, filed Sept. 30, 1975 now U.S. Pat. No. 4,084,954.

BACKGROUND OF THE INVENTION

This invention relates generally to new and useful biocidally active compounds. More specifically, it relates to novel 1,3-benzodithiole-2-one and 1,3-benzodithiole-2-thione compounds prepared by an unusual but highly simple and convenient cyclization reaction. In fact, it is due to this synthesis that the numerous derivatives disclosed herein can be obtained so easily and in good yields.

The novel compounds of this invention are useful in treating pests associated with growing plants in order to beneficially enhance the growth and/or yield-potential of said growing plants. This is accomplished by applying a biocidally active amount of the subject compound to soil, seed or the growing plant. The term "pests" as used herein is meant to include plant pests such as weeds and fungi, and animal pests such as arachnids, nematodes, or insects.

The concentration, rate and physical form of the administered compound are determined by the particular application, said application comprising one or more of the following:
(1) herbicidal
(2) fungicidal
(3) acaricidal
(4) nematocidal
(5) insecticidal Generally, for each particular application, there will be a preferred range with respect to concentration, a preferred amount with respect to rate and a preferred type with respect to formulation.

For purposes of this disclosure and for the sake of convenience and clarity, certain terms used herein are defined as follows:

The phrase "treating pests associated with growing plants" signifies the application of a compound as herein defined to pests associated with growing plants which embraces germinating plants, e.g. seeds, sprouts, seedlings, and fully grown plants. The mode of application will depend on the desired end use. For example, if the treatment is for pre-emergent herbicidal use, the compound will be administered into the soil which contains the growing seeds. In contrast, when used as a post-emergent herbicide, the compound will be applied to the growing plants after seeds have germinated.

When treatment comprises foliar fungicidal application, the compound is administered, as a spray, directly onto the leaves and other above ground portions of diseased plants.

For use as an acaricide, the compound may be applied by contacting the leaves (or plant) directly or as a soil incorporation in the soil where the plant is growing.

For use as a soil or seed treatment fungicide, the compound is usually applied as a seed treatment, or as a drench and/or incorporation to the soil containing the seed or the growing plant.

For use as a nematocide, the compound is normally applied directly as a drench and/or incorporation to the soil containing the growing plant.

For use as an insecticide, the compound is usually applied topically to the above ground portions of infested plants and/or to the soil containing the growing plants.

All of the aforesaid treatments, whatever the objective, have a unitary result. That is, they beneficially enhance or improve the growth and/or yield potential of the treated plant.

The term "biocidally active amount" means an amount of compound which effectively permits the desired objective.

SUMMARY OF THE INVENTION

Accordingly, this invention is concerned with compounds of the formula:

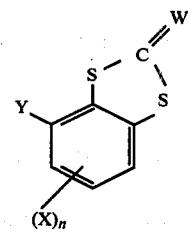

wherein W is O or S; Y is selected from hydrogen, cyano, alkylsulfonyl, nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, N-morpholino, N-piperidino, N-piperazino, N-pyrrolidino, dimethylaminodithiocarbamyl, carboalkoxy, alkylthio, mono- and di-alkylamino, N-alkylcarbamyl, N,N-dialkylcarbamyl, alkylsulfoxy, alkylsulfonyl, said alkyl groups containing from 1 to 4 carbon atoms; n is an integer from 0 to 3; and salts thereof.

Of particular interest are compounds as shown above wherein W is O, Y is nitro and n is 1, such as:
6-methyl-4-nitro-1,3-benzodithiole-2-one
4-nitro-6-trifluoromethyl-1,3-benzodithiole-2-one
4,6-dinitro-1,3-benzodithiole-2-one
6-fluoro-4-nitro-1,3-benzodithiole-2-one
6-chloro-4-nitro-1,3-benzodithiole-2-one
6-cyano-4-nitro-1,3-benzodithiole-2-one.

Other preferred compounds include those as shown above wherein W is O, Y is nitro and n is 2 such as:
6-chloro-7-methyl-4-nitro-1,3-benzodithiole-2-one
7-dimethylaminodithiocarbamyl-4-nitro-6-trifluoromethyl-1,3-benzodithiole-2-one
7-chloro-4-nitro-6-trifluoromethyl-1,3-benzodithiole-2-one.

Still others which are preferred as those as shown above wherein W is O, Y is nitro and n is 3 such as:
5,7-dimethyl-4,6-dinitro-1,3-benzodithiole-2-one.

Another compound which is preferred as shown above wherein W is O, Y is nitro and n is 0 is:
4-nitro-1,3-benzodithiole-2-one.

Still others which are preferred are those as shown above wherein W is O, Y is trifluoromethyl and n is 1 such as:

6-nitro-4-trifluoromethyl-1,3-benzodithiole-2-one.

Still others which are preferred are those as shown above wherein W is O, Y is trifluoromethyl and n is 2 such as:

7-di-n-propylamino-6-nitro-4-trifluoromethyl-1,3-benzodithiole-2-one 7-monoisopropylamino-6-nitro-4-trifluoromethyl-1,3-benzodithiole-2-one 7-mono-n-propylamino-6-nitro-4-trifluoromethyl-1,3-benzodithiole-2-one 7-diethylamino-6-nitro-4-trifluoromethyl-1,3-benzodithiole-2-one 7-n-propylthio-6-nitro-4-trifluoromethyl-1,3-benzodithiole-2-one 7-isopropylthio-6-nitro-4-trifluoromethyl-1,3-benzodithiole-2-one 7-diallylamino-6-nitro-4-trifluoromethyl-1,3-benzodithiole-2-one 7-methylamino-6-nitro-4-trifluoromethyl-1,3-benzodithiole-2-one 7-monobutylamino-6-nitro-4-trifluoromethyl-1,3-benzodithiole-2-one 7-dibutylamino-6-nitro-4-trifluoromethyl-1,3-benzodithiole-2-one 7-monophenylamino-6-nitro-4-trifluoromethyl-1,3-benzodithiole-2-one 6-nitro-7-piperidino-4-trifluoromethyl-1,3-benzodithiole-2-one 7-morpholino-6-nitro-4-trifluoromethyl-1,3-benzodithiole-2-one 6-nitro-7-pyrrolidino-4-trifluoromethyl-1,3-benzodithiole-2-one.

Still others which are preferred are those as shown above wherein W is O, Y is trifluoromethyl and n is 3.

Still others which are preferred are those as shown above wherein W is S, Y is nitro and n is 1 such as:

4-nitro-6-trifluoromethyl-1,3-benzodithiole-2-thione 6-methyl-4-nitro-1,3-benzodithiole-2-thione.

Still others which are preferred are those as shown above wherein W is O, Y is hydrogen and n is 1 such as:

5-nitro-1,3-benzodithiole-2-one 5-trifluoromethyl-1,3-benzodithiole-2-one.

Also within the purview of this invention is the novel process for preparing such compounds involving a unique cyclization step as well as the use of such compounds to beneficially enhance the growth and/or yield-potential of plants.

DETAILED DESCRIPTION OF THE INVENTION

The novel compounds of this invention are prepared by a novel procedure wherein a unique cyclization step is involved. It is this synthetic method which allows for the formation of the numerous compounds disclosed herein. Compounds which would ordinarily be inaccessible or at best, tedious and difficult to make, are rendered available by an unusually simple and mild synthesis.

The process can be expressed by the following reactions:

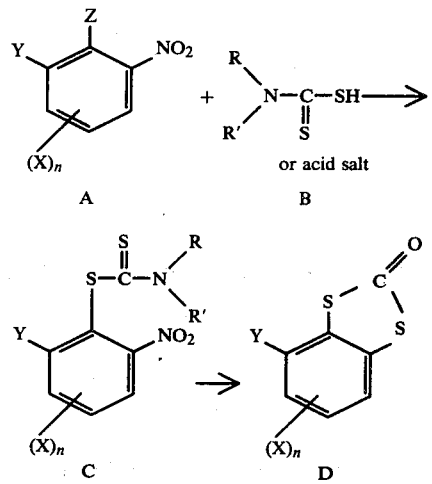

wherein Y is selected from hydrogen, cyano, alkylsulfonyl, nitro and trifluoromethyl; X is selected from alkyl and alkenyl of up to 6 carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, N-morpholino, N-piperidino, N-piperazino, N-pyrrolidino, dimethylaminodithiocarbamyl, carboalkoxy, alkylthio, mono- and dialkylamino, N-alkylcarbamyl, N,N-dialkylcarbamyl, alkylsulfoxy, alkylsulfonyl, said alkyl groups containing from 1 to 4 carbon atoms and n is an integer from 0 to 3; Z is halogen (F, Cl, Br, I) or alkoxy, and R and R' are each alkyl groups, straight- or branch-chained, containing from 1 to 4 carbon atoms.

Starting material A is typically a halobenzene derivative, many of which are commercially available. If not, one can easily synthesize the desired compound using well-documented chemical techniques. As is apparent, the halo group (Z) and the adjacent nitro group both undergo substitution thereby effecting cyclization to form the heterocyclic 5-membered ring. The other reagent, B, is an N,N-dialkyldithiocarbamic acid or acid salt, such as the sodium salt.

The attractiveness of the above process is that under relatively mild conditions, using generally available or easily accessible reagents and in a single step, one can obtain the desired compounds in good yields. The intermediate product C of this reaction can in many preparations be isolated. In others it undergoes the cyclization reaction, even at low temperatures, to produce final product D, the substituted 1,3-benzodithiole-2-ones.

The novelty of this synthetic method is clearly evident to one skilled in the art. It enables one to fuse onto a benzene ring containing adjacent nitro and halo groups a cyclic ring having the structure:

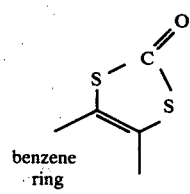

benzene ring

Importantly, it allows one to do this under mild conditions and using various chlorobenzene derivatives so that almost any desired substituted compound results.

The reaction process is carried out in the temperature range of from 0° C. to 200° C. In many instances, the reaction proceeds at room temperature or lower, whereas, in some cases, elevated temperatures may be desired in order to accelerate the reaction.

The reaction is usually carried out in a solvent, although the solvent may be omitted if effective dissolution of materials is possible. A solvent is generally preferred, however, and it can be any solvent which does not enter into the reaction and in which the reactants are soluble to some extent. Suitable solvents are dimethylformamide, dimethylsulfoxide, acetone and methyl isobutyl ketone.

The mole ratio of reagents A and B is normally 1 to 1, however, it is generally preferred to use a slight excess of reagent B to ensure more complete reaction.

A co-product E is usually formed during the formation of desired product D. This co-product is easily separated from product D using solvent differential properties. It is converted to compound D by treatment under basic conditions, such as sodium hydroxide in an aqueous solution or suspension containing solvent. A typical solvent for such conversion is dimethylsulfoxide.

The reaction is carried out at temperatures ranging from 0° to 200° C. The work-up is standard—product is obtained by precipitation, washing, drying and recrystallization if necessary.

The 1,3-benzodithiole-2-thione compounds disclosed herein are obtained by conversion of the corresponding 1,3-benzodithiole-2-one compounds. The conversion of >C=O to >C=S is well-known in the chemical literature and several ways are available for effecting it.

One way uses disodium trithiocarbonate as the sulfurizing agent. Other suitable reagents include sodium hydrosulfide and potassium thiocyanate.

The biocidal processes of this invention comprise applying a biocidally effective amount of a compound disclosed herein to soil, seed or growing plant. The compounds are formulated for use either as sprays made up by adding an inert diluent such as water to emulsifiable concentrates or wettable powders, as granules or as dispersions on carriers such as attapulgite clay granules, peat moss, fertilizer, vermiculite, etc. The compounds are quite insoluble in water, and hence, for the preparation of emulsions or wettable powders, the compounds are preferably formulated with wetting agents.

Since numerous compounds disclosed herein are free bases and acids, they can be converted to acid salts (free bases) and base salts (free acids).

The acid-addition and base-addition salts are within the purview of this invention. The acid-addition salts are easily prepared by treating the amine base with a substantially equimolar amount of a chosen acid in an aqueous solution or in a suitable organic solvent such as methanol or ethanol. The only restriction on the acid used is that it provides acceptable ions, i.e., those which do not deleteriously affect the growing plants. The base-addition salts are prepared in a similar manner except that base instead of acid is added. The same restriction with respect to acceptable ions applies.

For herbicidal use, the compounds disclosed herein are applied at a rate of from 0.5 lbs a.i./acre to 8.0 lbs a.i./acre.

For soil fungicidal use, the compounds disclosed herein are applied at a rate of from 0.25 to 40.0 lbs a.i./acre.

For seed treatment fungicidal use the compounds disclosed herein are applied at a rate of from 2.0 to 10.0 ounces per 100 lbs. of crop seed.

For foliar fungicidal use, the compounds disclosed herein are applied at a rate of about 200 parts per million in a suitable solvent, such as water.

For acaricidal use, the compounds disclosed herein are applied at a rate of from 30 to 1000 parts per million in a suitable solvent, such as water.

For nematocidal use, the compounds disclosed herein are applied at a rate of from 15 to 20 parts per million in a suitable solvent, such as water.

For insecticidal use, the compounds disclosed herein are applied at a rate of from 0.2% to 10.0% in a suitable solvent, such as water.

EXAMPLE I

4-Nitro-6-trifluoromethyl-1,3-benzodithiole-2-one

To a magnetically stirred solution of 2,6-dinitro-4-trifluoromethyl-chlorobenzene (445 g., 1.65 M) in acetone (3300 ml.) was added N,N-dimethyldithiocarbamic acid sodium salt dihydrate (295 g., 1.65 M) and the reaction mixture was maintained at 0°–5° C. during addition.

After addition, the reaction mixture was stirred at 5°–10° C. for 90 minutes and thereafter for 18 hours at room temperature.

The acetone-insoluble solids were suction filtered, washed well with water, dried and soxhlet-extracted with hexane overnight. The hexane extract was stripped free of solvent on a rotary evaporator under vacuum yielding 6.5 g. of desired product. A co-product (223.4 g., M.P. 222°–224° C.) remained unextracted.

The acetone filtrate was stripped free of solvent under vacuum and the residual solid washed with ethanol (100 ml.) and suction filtered. The solid was soxhlet extracted with hexane overnight. Removal of solvent from the hexane extract yielded the desired product (188.5 g., 40.7% theory, M.P. 110°–111° C.).

EXAMPLE II

Conversion of the co-product of Example I to 4-nitro-6-trifluoromethyl-1,3-benzodithiole-2-one To a stirred suspension of the co-product from Example I (3.26 g.) in dimethylsulfoxide (30 ml.) was added a solution of NaOH (0.88 g., 0.022 M) dimethylsulfoxide (15 ml.) and water (5 ml.). The reaction mixture was allowed to stir at room temperature under nitrogen gas for 22 hours.

The resulting solution was poured into water (300 ml.), made acidic by addition of conc. HCl, solid filtered off, washed with water and dried. Recrystallization from hot hexane yielded pure 4-nitro-6-trifluoromethyl-1,3-benzodithiole-2-one. (Confirmed by mixed M.P. and I.R. spectra).

EXAMPLE III

Conversion of 4-Nitro-6-trifluoromethyl-1,3-benzodithiole-2-one to 4-nitro-6-trifluoromethyl-1,3-benzodithiole-2-thione To a stirred and cooled solution of 4-nitro-6-trifluoromethyl-1,3-benzodithiole-2-one (14.05 g., 0.05 M) in DMSO (150 ml.) was added dropwise a solution of disodium trithiocarbonate (48.15 g., 0.12 M of 40% aqueous solution). The reaction mixture was permitted to stir for 60 minutes at about 15° C. and thereafter for 2½ hours at ambient temperatures.

The resulting solution was poured into an excess of water, acidified and extracted with chloroform (3×100 ml.). The organic layer was separated, dried, stripped free of solvent and chromatographed over silica gel. Elution with hexane removes elemental sulfur. Another elution with hexane yields the desired product. (4.5 g., 30.3% theory, M.P. 109.5°–110.5° C.).

EXAMPLE IV

The procedure of Example I is repeated wherein the following chlorobenzene derivatives are used in place of 2-6-dinitro-4-trifluoromethylchlorobenzene to provide the corresponding products:

| chlorobenzene derivative | Product |
| --- | --- |
| 2,6-dinitro-4-methyl-chlorobenzene | methyl-4-nitro-1,3-benzodithiole-2-one M.P. 163–164° C. |
| 2,4,6-trinitro-chlorobenzene | 4,6-dinitro-1,3-benzoidithiole-2-one M.P. 129–131° C. |
| 2,6-dinitro-4-fluoro-chlorobenzene | 6-fluoro-4-nitro-1,3-benzodithiole-2-one M.P. 98–100° C. |
| 4-chloro-2,6-dinitro-chlorobenzene | 6-chloro-4-nitro-1,3-benzodithiole-2-one M.P. 152–153° C. |
| 1,4-dichloro-3-methyl-2,6-dinitro-chlorobenzene | 6-chloro-7-methyl-4-nitro-1,3-benzodithiole-2-one M.P. 147–148° C. |
| 3-chloro-2,6-dinitro-4-trifluoromethylchlorobenzene | 7-dimethylaminodithiocarbamyl-4-nitro-6-trifluoromethyl-1,3-benzodithiole-2-one M.P. 138–141° C. |
| 3-chloro-2,6-dinitro-4-trifluoromethylchlorobenzene | 7-chloro-nitro-6-trifluoro-methyl-1,3-benzodithiole-2-one M.P. 87–89° C. |
| 2,6-dinitrochlorobenzene | 4-nitro-1,3-benzodithiole-2-one M.P. 110–111° C. |
| 3,5-dimethyl-2,4,6-trinitro-chlorobenzene | 5,7-dimethyl-4,6-dinitro-1,3-benzodithiole-2-one M.P. 130–131° C. |
| 2,4-dinitro-6-trifluoromethyl-chlorobenzene | 6-nitro-4-trifluoromethyl-1,3-benzodithiole-2-one M.P. 117–118.5° C. |
| 3-di-n-propylamino-2,4-dinitro-6-trifluoromethyl-chlorobenzene | 7-di-n-propylamino-6-nitro-4-trifluoromethyl-benzodithiole-2-one M.P. 60–61° C. |
| 2,4-dinitro-3-monoisopropyl-amino-6-trifluoromethyl-chlorobenzene | 7-monoisopropylamino-6-4-trifluoromethyl-1,3-benzodithiole-2-one M.P. 71.5–72.5° C. |
| 2,4-dinitro-3-mono-n-propyl-amino-6-trifluoromethyl-chlorobenzene | 7-monopropylamino-6-nitro-4-trifluoromethyl-1,3-benzodithiole-2-one M.P. 72–74° C. |
| 3-diethylamino-2,4-dinitro-6-trifluoromethylchlorobenzene | 7-diethylamino-6-nitro-4-trifluoromethyl-1,3-benzodithole-2-one M.P. 61–63° C. |
| 2,4-dinitro-3-n-propylthio-6-trifluoromethylchlorobenzene | 6-nitro-7-n-propylthio-4-trifluoromethyl-1,3-benzodithole-2-one M.P. 90–91° C. |
| 2,4-dinitro-3-isopropylthio-6-trifluoromethylchlorobenzene | 7-isopropylthio-6-nitro-4-trifluoromethyl-1,3-benzodithiole-2-one M.P. 79.5–80.5° C. |
| 4-cyano-2,6-dinitrochlorobenzene | 6-cyano-4-nitro-1,3-benzodithiole-2-one M.P. 173–175° C. |
| 3-diallylamino-2,4-dinitro-6-trifluoromethylchlorobenzene | 7-diallylamino-6-nitro-4-trifluoromethyl-1,3-benzoidithiole-2-one a liquid |
| 2,4-dinitro-3-methylamino-6-trifluoromethylchlorobenzene | 7-methylamino-6-nitro-4-trifluoromethyl-1,3-benzodithiole-2-one M.P. 171–173° C. |
| 2,4-dinitro-3-monobutylamino-6-trifluoromethylchlorobenzene | 7-mono-n-butylamino-6-nitro-4-trifluoromethyl-dithiole-2-one 1,3-benzodithiole-2-one a liquid |
| 3-dibutylamino-2,4-dinitro-6-trifluoromethylchlorobenzene | 7-di-n-butylamino-6-nitro-4-trifluoromethyl-1,3-benzo-dithiole-2-one a liquid |
| 2,4-dinitro-3-monophenylamino-6-trifluoromethylchlorobenzene | 7-monophenylamino-6-nitro-4-trifluoromethyl-1,3-benzo-dithiole-2-one M.P. 121–122° C. |
| 2,4-dinitro-3-piperidino-6-trifluoromethylchlorobenzene | 6-nitro-7-piperidino-4-trifluoromethyl-1,3-benzo-dithiole-2-one M.P. 155–157° C. |
| 2,4-dinitro-3-morpholino-6-trifluoromethylchlorobenzene | 7-morpholino-6-nitro-4-trifluoromethyl-1,3-benzo-dithiole-2-one M.P. 178–180° C. |
| 2,4-dinitro-pyrrolidino-6-trifluoromethylchlorobenzene | 6-nitro-7-pyrrolidino-4-trifluoromethyl-1,3-benzodi thiole-2-one M.P. 104–105° C. |
| 2,4-dinitrochlorobenzene | 6-nitro-1,3-benzodithiole-2-one M.P. 131–136° C. |
| 2-nitro-4-trifluoromethyl-chlorobenzene | 5-trifluoromethyl-1,3-benzo-dithiole-2-one M. P. 36–42° C. |

EXAMPLE V

The compounds enumerated in Example IV are converted to the corresponding 1,3-benzodithiole-2-thiones in accordance with the procedure outlined in Example III.

EXAMPLE VI

The procedure of Example I is repeated wherein the following N,N-dialkyldithiocarbamic acid compounds in stoichiometric equivalent amounts are used in place of N,N-dimethyldithiocarbamic acid sodium salt dihydrate with comparable results:
  N,N-dimethyldithiocarbamic acid potassium salt
  N,N-diethyldithiocarbamic acid sodium salt
  N,N-diisopropyldithiocarbamic acid sodium salt
  N,N-dibutyldithiocarbamic acid sodium salt
  N-ethyl-N-methyldithiocarbamic acid sodium salt

EXAMPLE VII

The procedure of Example I is repeated wherein the following solvents are used in place of acetone with comparable results:
  dimethylsulfoxide
  dimethylformamide
  methylisobutyl ketone

EXAMPLE VIII

The compound of Example I is prepared in the following manner: To a magnetically stirred solution of 16.2 g (60 mmoles) 2,6-dinitro-4-trifluoromethylchlorobenzene in 60 ml dimethylsulfoxide was added dropwise a solution of 10.74 g (60 mmoles) sodium dimethyldithiocarbamic acid. The reaction is mildly exothermic and accompanied by evolution of oxides of nitrogen. After allowing the reaction mixture to stir for 3 hours, 450 ml water and 225 ml chloroform are added and, after shaking well in an extraction funnel, the chloroform extract was withdrawn and the aqueous phase similarly extracted with two more 220 ml portions of chloroform. The combined chloroform extract was washed thrice with 750 ml portions of water, and dried over anhy. $Na_2SO_4$. After removing the solvent on a rotary evaporator, the residue was chromatographed over 180 g Silica-Gel. Elution with hexane-benzene (1:1) yielded 7.3 g (43.3%) 4-nitro-6-trifluoromethyl-1,3-benzodithiole-2-one, m.p. 103°–107° C. One recrystallization from ethanol yielded product, m.p. 111°–112° C.

Elemental Analyses % Found: C=33.9; H=0.9; N=4.9; % Calc: C=34.2; H=0.71; N=5.0.

NMR ($CDCl_3$): 8.16 δ (1H, m); 8.6 δ (1H, m)

EXAMPLE IX

The procedure of Example VIII is repeated wherein the following halobenzene derivatives are used in place of 2,6-dinitro-4-trifluoromethylchlorobenzene to provide corresponding products:

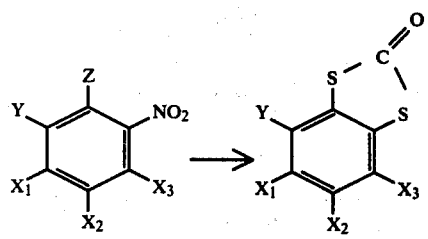

| halobenzene derivative | | | | |
|---|---|---|---|---|
| Z | Y | $X_1$ | $X_2$ | $X_3$ |
| Cl | $NO_2$ | allyl | H | H |
| Br | $NO_2$ | hexyl | H | H |
| F | $NO_2$ | H | $CCl_3$ | H |
| Cl | $NO_2$ | H | $CF_3O$ | H |
| Cl | $CF_3$ | H | $CH_3SO_2$ | H |
| Cl | $NO_2$ | H | $CF_3S$ | H |
| Cl | $NO_2$ | H | $CF_3SO$ | H |
| Cl | $NO_2$ | H | CN | H |
| Cl | $NO_2$ | H | $CF_3SO_2$ | H |
| Cl | $NO_2$ | H | H | H |
| Cl | $NO_2$ | H | $CH_3OCH_2$ | H |
| Cl | $CF_2$ | H | CN | H |
| Cl | $CF_3$ | H | COOH | H |
| Cl | $CF_3$ | H | OH | H |
| Cl | $CF_3$ | H | $NH_2$ | H |

EXAMPLE X

For determination of herbicidal activity for the herein disclosed compounds, the following screen was used: The candidate compound is applied at 8 lb/A in 40 gal/A to one foot square flats containing seeds or plants of the test plant species. Visual ratings of phytotoxicity are made after 7 and 14 days. The phytotoxicity rating system is based on 0=no control and 10=complete kill or 100% control.

For post emergent use, the flats are planted with the desired plant species 7-9 days prior to spraying. By spraying time a well established flat of plants is ready for spraying. For incorporated pre-emergence use, the flats are prepared and planted with seed of the various species. A sheet of plastic is then placed over the seed and a measured quantity of screened soil normally used for covering the seed is placed on top. The flat is then ready for spraying. After spraying, the soil on top of the sheet of plastic is mixed thoroughly and spread evenly over the surface of the flat.

The plant species used in herbicide screening are corn (*Zea mays* L.), wheat (*Triticum avesticum* L.), cotton (*Gossypium hirsutum* L), soybeans (*Glycine max* L.), barnyardgrass (*Echinochlo acrusgalli* L. Beauv), foxtail (*Setaria viridis* L. Beauv), morningglory (*Ipomea purpurea* L. Roth), and pigweed (*Amaranthus retroflexus* L.).

The following compounds exhibited herbicidal properties:

7-di-n-propylamino-6-nitro-4-trifluoromethyl-1,3-benzodithiole-2-one 7-diethylamino-6-nitro-4-trifluoromethyl-1,3-benzodithiole-2-one 7-diallylamino-6-nitro-4-trifluoromethyl-1,3-benzodithiole-2-one

EXAMPLE XI

For determination of soil fungicidal activity for the herein disclosed compounds, the following screen was used: Two potato-dextrose-agar plates of the desired fungal organism are blended in a Waring blender with 50 mls of sterile water. The resulting mixture is added to 3000 g of sterile soil in a plastic bag and thoroughly blended. Cucumber seeds are planted in 4 oz. cups containing a measured amount of the inoculated soil mixture. Finally, 10 mls of the candidate compound at 40 lb/A is atomized as a drench over the prepared soil. After 14 days evaluations are made based on the number of surviving seedlings in the treated cup compared to the untreated check.

The organisms used in the primary soil fungicide screen are *Rhizoctonia solani* and *Pythium ultimum.*

The following compounds exhibited soil fungicidal properties:

4-nitro-6-trifluoromethyl-1,3-benzodithiole-2-one 4-nitro-1,3-benzodithiole-2-one 6-fluoro-4-nitro-1,3-benzodithiole-2-one 7-chloro-4-nitro-6-trifluoromethyl-1,3-benzodithiole-2-one 7-monoisopropylamino-6-nitro-4-trifluoromethyl-1,3-benzodithiole-2-one 7-mono-n-propylamino-6-nitro-4-trifluoromethyl-1,3-benzodithiole-2-one 7-diethylamino-6-nitro-4-trifluoromethyl-1,3-benzodithiole-2-one 7-methylamino-6-nitro-4-trifluoromethyl-1,3-benzodithiole-2-one 6-nitro-7-piperidino-4-trifluoromethyl-1,3-benzodithiole-2-one 7-n-propylthio-6-nitro-4-trifluoromethyl-1,3-benzodithiole-2-one 7-isopropylthio-6-nitro-4-trifluoromethyl-1,3-benzodithiole-2-one 4-nitro-6-trifluoromethyl-1,3-benzodithiole-2-thione 7-dimethylaminodithiocarbamyl-4-nitro-6-trifluoromethyl-1,3-benzodithiole-2-one 5-trifluoromethyl-1,3-benzodithiole-2-one
1,3-benzodithiole-2-one
1,3-benzodithiole-2-thione

EXAMPLE XII

For determination of foliar fungicidal activity for the herein disclosed compounds, the following screen was used. The candidate compound is applied at 200 ppm to Bonny Best variety of tomato plants which have 2–4 true leaves. The treated plants are held at a relative humidity of 100% for 48 hours allowing ideal conditions for fungal invasion to occur. The plants are removed to the greenhouse bench and held for 7–10 days after which visual ratings are made. Ratings are by Infection Index (I I) where $_x$O=no infection or 100% control, and 10=100% infection or no control.

To inoculate the plants, a spore suspension of early blight fungus (*Alternaria solani*) is prepared and sprayed on the plant until it reaches the point of runoff.

The following compounds exhibited foliar fungicidal properties:
 4-nitro-6-trifluoromethyl-1,3-benzodithiole-2-one
 4,6-dinitro-1,3-benzodithiole-2-one
 5-trifluoromethyl-1,3-benzodithiole-2-one
 1,3-benzodithiole-2-one
 6-cyano-4-nitro-1,3-benzodithiole-2-one

EXAMPLE XIII

For determination of acaricidal activity for the herein disclosed compounds, the following screening procedure was used: To evaluate a compound as a contact acaricide, the solution is sprayed at 15 psi onto the leaves of bean seedlings infested with mites as a 0.1% concentration. The sprayed plants are inoculated 24 hours later. In the case of systemic testing, the chemical is added to the nutrient solution in which the bean seedling is growing at a concentration of 20 ppm. After three days, mites are added to the leaves grown in the treated solution. In both cases, five days later counts are made and percent kill determined.

Two spotted spider mites (*Tetranychus urticae*) are used in these tests and pinto beans (*Phaseolus vulgaris*) in the cotylendonary stage is the host plant species used.

The following compounds exhibited acaricidal properties:
 4-nitro-6-trifluoromethyl-1,3-benzodithiole-2-one
 4,6-dinitro-1,3-benzodithiole-2-one
 6-methyl-4-nitro-1,3-benzodithiole-2-one
 4-nitro-1,3-benzodithiole-2-one
 6-fluoro-4-nitro-1,3-benzodithiole-2-one
 7-chloro-4-nitro-6-trifluoromethyl-1,3-benzodithiole-2-one
 7-di-n-propylamino-6-nitro-4-trifluoromethyl-1,3-benzodithiole-2-one
 7-monoisopropylamino-6-nitro-4-trifluoromethyl-1,3-benzodithiole-2-one
 7-monopropylamino-6-nitro-4-trifluoromethyl-1,3-benzodithiole-2-one
 7-diethylamino-6-nitro-4-trifluoromethyl-1,3-benzodithiole-2-one
 7-methylamino-6-nitro-4-trifluoromethyl-1,3-benzodithiole-2-one
 7-mono-n-butylamino-6-nitro-4-trifluoromethyl-1,3-benzodithiole-2-one
 7-diallylamino-6-nitro-4-trifluoromethyl-1,3-benzodithiole-2-one
 6-nitro-7-n-propylthio-4-trifluoromethyl-1,3-benzodithiole-2-one
 7-isopropylthio-6-nitro-4-trifluoromethyl-1,3-benzodithiole-2-one
 4-nitro-6-trifluoromethyl-1,3-benzodithiole-2-thione
 5-nitro-1,3-benzodithiole-2-one
 5-trifluoromethyl-1,3-benzodithiole-2-one
 1,3-benzodithiole-2-thione.

EXAMPLE XIV

For determination of nematocidal activity for the herein disclosed compounds, the following screening procedure was used: The roots of established tomato plants, grown in the presence of root knot (*Meloidogyne incognita*) nematodes and with adequately galled roots, are cut into small segments. The root segments are added to sterile soil and thoroughly mixed. The root knot infested soil is allowed to set for three days. During this period many larva will emerge from the decaying plant roots yielding a high potential of root knot inoculum soil. A quantity of the soil mixture is added to 8 oz. cups. Finally, 10 mls of the candidate nematocide at 20 ppm is added to the infested soil and thoroughly blended. The treated soil is removed from the jar and placed in an 8 oz. cup. The treated soil is allowed to aerate for 48 hours. Finally, cucumber seeds are planted in the treated soil. After 3–4 weeks, evaluations are made based on the galls occurring on the developing cucumber seedlings. The system used is the Root-Knot Index (RKI) based on a 0–10 rating where 0=No galls and 10=100% galling.

The following compounds exhibited nematocidal properties:
 4-nitro-6-trifluoromethyl-1,3-benzodithiole-2-one
 4,6-dinitro-1,3-benzodithiole-2-one
 6-methyl-4-nitro-1,3-benzodithiole-2-one
 4-nitro-1,3-benzodithiole-2-one
 6-fluoro-4-nitro-1,3-benzodithiole-2-one
 5-nitro-1,3-benzodithiole-2-one.

EXAMPLE XV

For determination of insecticidal activity for the herein disclosed compounds, the following screening procedure was used:

A. Screwworm Test

The candidate compound was evaluated as an insecticide on screwworms at rates of 0.3125–10.0%. The solutions were applied on 1st, 2nd, and 3rd instar larvi and on eggs.

Two reps on each larvi instar and the eggs were placed on black filter paper in petri dishes and sprayed with 5 ml total volume at each concentration. Ratings were made 48 hours following application.

B. White Fly Test

White fly infested tobacco (Nicotiana) plants were sprayed with a 1% solution of candidate test compound. Within 12 hours after application of the chemical, all white flies were either dead or had left the tobacco plants. White fly populations were too large to make quantitative counts, so visual observations were made.

The following compound exhibited insecticidal properties in A and B above:
 4-nitro-6-trifluoromethyl-1,3-benzodithiole-2-one

C. Pea Aphid Test

The candidate compounds were applied in a 0.5% solution to pea aphids and pea seedling plants in a contact test using a Waters vertical spray tower. The spray descends through an 8 inch stainless steel cylinder to the test insects and plants 44 inches below the atomizer. The spray tower is operated at 10 p.s.i. and discharges about 30 milliliters of spray per minute through a Devilbiss atomizer. The insects and seedlings were sprayed for a 15 second period and held for forty-eight hour mortality determinations.

D. Southern Armyworm Test

Excised lima bean leaves were dipped into 0.05% solutions of the candidate compounds and when dry were offered to 10 larvae of the Southern armyworm (late third instar) for a 48 hour feeding period.

The following compounds exhibited insecticidal properties in C and D above:
4-nitro-6-trifluoromethyl-1,3-benzodithiole-2-one
6-fluoro-4-nitro-1,3-benzodithiole-2-one
7-chloro-4-nitro-6-trifluoromethyl-1,3-benzodithiole-2-one
6-nitro-4-trifluoromethyl-1,3-benzodithiole-2-one It should be understood by those skilled in the art that various modifications may be made in the present invention without departing from the spirit and scope thereof as described in the specification and defined in the appended claims.

What is claimed is:

1. A compound selected from the group consisting of those of the formula:

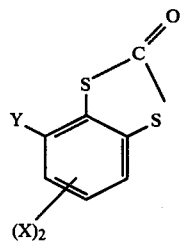

wherein Y is selected from nitro and trifluoromethyl; each X independently is selected from alkyl and alkenyl of up to six carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, dimethylaminodithiocarbamyl, carboalkoxy, alkylthio, mono- and dialkylamino, N-alkylcarbamyl, N,N-dialkylcarbamyl, alkylsulfoxy, alkylsulfonyl, N-morpholino, N-piperidino, N-piperazino or N-pyrrolidino, said alkyl and alkoxy groups containing from 1 to 4 carbon atoms, wherein at least one of said X groups is selected from N-morpholino, N-piperidino, N-piperazino or N-pyrrolidino; and a salt thereof.

2. The compound as claimed in claim 1 which is 6-nitro-7-piperidino-4-trifluoromethyl-1,3-benzodithiole-2-one.

3. The compound as claimed in claim 1 which is 7-morpholino-6-nitro-4-trifluoromethyl-1,3-benzodithiole-2-one.

4. The compound as claimed in claim 1 which is 6-nitro-7-pyrrolidino-4-trifluoromethyl-1,3-benzodithiole-2-one.

5. A soil fungicidal composition comprising an effective soil fungicidal amount of a compound as claimed in claim 1 and an inert diluent therefor.

6. A method of treating soil fungi associated with growing plants to beneficially enhance the growth and/or yield-potential of said growing plants which comprises applying a soil fungicidally active amount of a compound selected from the group consisting of those of the formula:

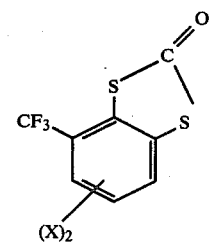

wherein each X independently is selected from alkyl and alkenyl of up to six carbon atoms, nitro, trichloromethyl, trifluoromethyl, trifluoromethoxy, trifluoromethylthio, trifluoromethylsulfoxyl, trifluoromethylsulfonyl, methoxymethyl, cyano, carboxy, carbamyl, halogen (F, Cl, Br, I), hydroxy, acetylamino, amino, N-phenylamino, N,N-diallylamino, alkoxy, dimethylaminodithiocarbamyl, carboalkoxy, alkylthio, mono- and dialkylamino, N-alkylcarbamyl, N,N-dialkylcarbamyl, alkylsulfoxy, alkylsulfonyl, N-morpholino, N-piperidino, N-piperazino, N-pyrrolidino, said alkyl and alkoxy groups containing from 1 to 4 carbon atoms, wherein at least one of said X groups is selected from N-morpholino, N-piperidino, N-piperazino or N-pyrrolidino; and salts thereof, at a rate of from 0.25 to 40.0 lbs. a.i./acre.

7. The method as claimed in claim 6 in which the compound is 6-nitro-7-piperidino-4-trifluoromethyl-1,3-benzodithiole-2-one.

8. The method as claimed in claim 6 in which the compound is 7-morpholino-6-nitro-4-trifluoromethyl-1,3-benzodithiole-2-one.

9. The method as claimed in claim 6 in which the compound is 6-nitro-7-pyrrolidino-4-trifluoromethyl-1,3-benzodithiole-2-one.

* * * * *